United States Patent [19]

Takiguchi et al.

[11] Patent Number: 4,973,160
[45] Date of Patent: Nov. 27, 1990

[54] SHG AUTOCORRELATOR

[76] Inventors: Yoshihiro Takiguchi, 3777 Independence Ave., Apt. 5G; Robert R. Alfano, 3777 Independence Ave., both of Bronx, N.Y. 10463; Yury Budansky, 484 Ramapo Valley Rd., Oakland, N.J. 07436

[21] Appl. No.: 334,029

[22] Filed: Apr. 6, 1989

[51] Int. Cl.[5] .............................. G01B 9/02
[52] U.S. Cl. ..................... 356/345; 356/346
[58] Field of Search ..................... 356/345, 346

[56] References Cited
U.S. PATENT DOCUMENTS 4,705,397 11/1987 Tsuchiya et al. ................. 356/345
4,792,230 12/1988 Naganuma et al. ............... 356/345

OTHER PUBLICATIONS

Fork et al., "Real-Time Intensity Interferometer", Applied Optics, vol. 17, No. 22, pp. 3534-3535, Nov. 1978.

Primary Examiner—Davis L. Willis
Assistant Examiner—Matthew W. Koren
Attorney, Agent, or Firm—Irving M. Kriegsman

[57] ABSTRACT

An SHG autocorrelator for use in measuring the duration of an ultrashort pulse of light includes in one embodiment a thin pellicle beamsplitter for splitting the pulse of light into first and second beams, a stationary optical delay disposed along the path of the first beam, a movable optical delay disposed along the path of the second beam, a thin SHG crystal, a concave mirror for bringing the first and second beams to focus into the SHG crystal, a photodetector for detecting light emitted from the SHG crystal, and a narrow bandpass filter in front of the photodetector for filtering out non second harmonic light. The device reduces time broadening and delay of ultrashort pulses in the femtosecond time domain.

18 Claims, 3 Drawing Sheets

SHG AUTOCORRELATOR

BACKGROUND OF THE INVENTION

The present invention relates generally to a technique for measuring pulse duration and coherence time of ultrashort light pulses using second harmonic generation (SHG) autocorrelators and more particularly to an SHG autocorrelator which does not introduce dispersion and therefore does not alter the pulse profile in time.

Recently, lasers have been developed which are able to generate laser pulses with pulse widths as short as about 6 femtoseconds (fs). For a number of reasons, it is desirable to be able to measure the pulse duration of such pulses.

A 6 fs laser pulse has a wide bandwidth on the order of 40 nanometers (nm) of the wavelength spread because of the uncertainty principle. The wide bandwidth will cause the pulse duration to change upon traveling through various media such as glass or liquids due to the wavelength dependence of the index of refraction. The pulse will be delayed and also be broadened in time because of the wavelength dependence of the index of refraction of the media.

The pulse delay arises from the dispersion of the group index of refraction which is expressed as follows using first order approximation:

$$\tau_{DELAY} = \frac{L}{c}\left[n_g\left(w_c - \frac{\Delta w}{2}\right) - n_g\left(w_c + \frac{\Delta w}{2}\right)\right]$$

where $\tau_{DELAY}$ is the time delay of the pulse, L is the thickness of the dispersive media, c is the velocity of light in a vacuum, $n_g(w)$ is the group index of refraction at wavelength w, $w_c$ is the wavelength at peak intensity and $\Delta w$ is the wavelength spread of the pulse. For example, a 1 millimeter (mm) thick element made of glass will cause a 10 fs pulse to be delayed by a factor of two times in pulse duration. For a crystal of KDP the time delay for pulses at 600 nanometers and 640 nanometers is:

$$\tau_{DELAY} = \frac{L}{c}(\eta_{g600} - \eta_{g640}) = L\,(1.427 \times 10^{-11}) \text{ seconds}$$

The pulse broadening in time because of the group dispersion effect can be expressed as follows:

$$\tau_{\frac{1}{2}}(L) = \sqrt{\tau_0^2 + \tau_D^2} = \tau_0\sqrt{\frac{1 + (4\ln\tau k''L)^2}{\tau_0} \cdot \frac{1}{\tau_0^2}}$$

(for gaussian pulses) where $\tau_0$ = input pulse full width at half maximum pulse duration.

$\tau_{\frac{1}{2}}(L)$ = output pulse duration after traveling a distance L in material:

$\tau_D = (4\ln 2k''L)^2$ = dispersion broadening of pulse width;

$$k'' = \text{dispersion} = \frac{\lambda^3}{2\pi c^2} \times \frac{\gamma^2 n}{\gamma \lambda^2}\,;$$

$\eta$ = phase index of refraction; and $\lambda$ = wavelength.

For example, for a 100 μm crystal of KDP, $\tau_{DELAY} = 1.43$ femtoseconds (fs) for 600 nm and 640 nm pulses.

The pulse broadening time $\tau_D$ for (BK−7) glass and for KDP is listed below for a 620 nm pulse for thicknesses of 100 μm, 10 μm and 5 μm. Also shown is the time broadening $\tau_{\frac{1}{2}}(L)$ for glass and KDP for $\tau_0 = 10$ fs for thicknesses of 100 μm and 10 μm.

| Thickness | $\tau_D$ Glass (BK-7) | $\tau_D$ KDP | $\tau_{\frac{1}{2}}(L)$ for $\tau_0 = 10$fs GLASS (BK-7) | $\tau_{\frac{1}{2}}(L)$ for $\tau_0 = 10$fs KDP |
|---|---|---|---|---|
| 100 μm | 1.645 fs | 1.648 fs | 10.13 fs | 10.13 fs |
| 10 μm | 0.164 fs | 0.1648 fs | 10.00 fs | 10.00 fs |
| 5 μm | 0.0823 fs | 0.0824 fs | 10.00 fs | 10.00 fs |

For 1 mm plates $\tau_{DELAY} = 14.3$ fs for glass and 14.3 fs for KDP and $\tau_D = 16.45$ fs for glass and 16.48 fs for KDP. For a 10 fs pulse input, $\tau_{\frac{1}{2}}(1\text{ mm}) = 19.25$ fs for BK−7 glass and 19.28 fs for KDP.

Typical dispersion factors are listed below for reference.

| | $\lambda$ | $\frac{\gamma\eta}{\gamma\lambda}$ | $\frac{d^2n}{d\lambda^2}$ |
|---|---|---|---|
| BK-7 GLASS | 600 | −37609.9 | 1.935 × 10¹¹ |
| | 610 | −35739.6 | 1.80720 × 10¹¹" |
| | 620 | −33992 | 1.6895 × 10¹¹" |
| | 630 | −32357.3 | 1.58146 × 10¹¹ |
| | 640 | −30,826.3 | 1.488 × 10¹¹ |
| KDP | 600 | −37645.4 | 1.93795 × 10¹¹ |
| | 610 | −35723 | 1.80962 × 10¹¹ |
| | 620 | −34023.1 | 1.6918 × 10¹¹ |
| | 630 | −32386.2 | 1.58348 × 10¹¹ |
| | 640 | −30.853.3 | 1.48373 × 10¹¹ |

In summation, the thickness of an element should be 100 microns or less to substantially reduce all effects from dispersion. Also, as the thickness increases the amount of dispersion will also increase.

One type of apparatus that is commonly used to measure the pulse duration of ultrashort light pulses is the SHG autocorrelator. In an SHG autocorrelator a pulse of light to be examined is split by a beamsplitter into two beams traveling along different paths. One beam is passed through a stationary optical delay and the other through an adjustable optical delay. The two beams are then combined by a lens in a second harmonic generating (SHG) crystal. The second harmonic pulse generated by the SHG crystal is then detected by a detector.

As can be appreciated, the beamsplitter, the lens and the SHG crystal in an SHG autocorrelator all cause the pulse duration to change due to group velocity dispersion. Thus, the apparatus will produce erroneous pulse duration measurements.

References of interest include Lasers For Ultrashort Light Pulses, J. Herrmann and B. Wilhelm, Chapter 3, North Holland Publishing, 1984; Biological Events Probed By Ultrafast Laser Spectroscopy, R. R. Alfano, Academic Press, Chapter 17, 1982; and Ultrashort Light Pulses, S. L. Shapiro, Springer Verlag, Volume 18, 1977.

It is an object of this invention to provide a new and improved SHG autocorrelator.

It is another object of this invention to provide an SHG autocorrelator in which the dispersion produced is minimized.

SUMMARY OF THE INVENTION

An SHG autocorrelator for use in measuring the duration of ultrashort pulses of light constructed according to the teachings of this invention comprises means for splitting a pulse of light into first and second beams, a first optical delay disposed along the path of the first beam, said first optical delay being adjustable, a second optical delay disposed along the path of the second beam for changing the direction of the second beam, a thin SHG crystal, curved mirror means for bringing the first and second beams to focus in the SHG crystal, and detector means for detecting light emitted from the SHG crystal.

In one embodiment of the invention, the means for splitting the ultrashort pulse of light into first and second beams comprises a thin pellicle (i.e. around 2.00 microns thick) type of beamsplitter. In another embodiment, the means for splitting the ultrashort pulse of light into first and second beams comprises a flat mirror and in a third embodiment the means for splitting the ultrashort pulse of light into first and second beams comprises a mirror coated corner cube.

In all embodiments, the various mirrors used i.e. the beamsplitting mirrors, the mirrors in the optical delays and the beam collecting (focusing) mirror, are all metal coated (rather than dielectric) type mirrors.

The SHG crystal used in the autocorrelator may be any nonlinear crystal having a $X^{(2)}$, where $X^{(2)}$ is the second order susceptability. Examples of materials that may be used for the crystal are KDP, KTP, $KNO_3$, $LiIO_3$, BBO and $LiNbNO_3$.

Various features and objects will appear from the description to follow. In the description, reference is made to the accompanying drawing which forms a part thereof, and in which is shown by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

The present invention is directed to an SHG autocorrelator in which time dispersion produced by the apparatus is minimized.

Figure 1:
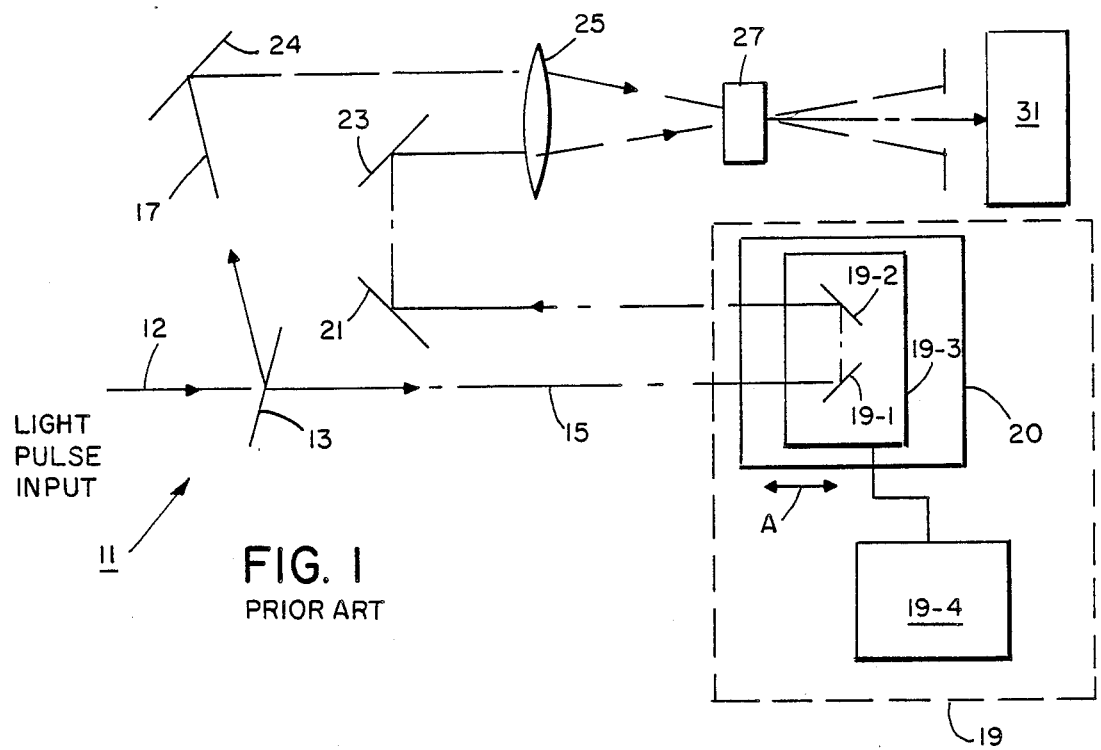
FIG. 1 is a schematic of a prior art SHG autocorrelator.

Referring now to the drawings, there is shown in FIG. 1 a schematic of a prior art SHG autocorrelator, the SHG autocorrelator being identified by reference numeral 11.

SHG autocorrelator 11 includes a beamsplitter 13 which splits an input pulse of light (from a source, not shown) into a transmitted beam 15 and a reflected beam 17. The transmitted beam 15 is passed through an optical delay 19 which is adjustable and then deflected off a pair of flat mirrors 21 and 23. Optical delay 19 comprises a pair of mirrors 19-1 and 19-2 which mounted on a support 19-3 which is movable on a base 20 in the direction shown by arrows A by a motor 19-4. Mirrors 21 and 23 are used to change the direction of beam 15. The beam 17 reflected by beamsplitter 13 is deflected off a stationary optical delay 24 which is in the form of a flat mirror. The light beams passed by the two optical delays 19 and 21 are collected by a lens 25 and brought to focus at the proper phase matching angle in a SHG crystal 27. Crystal 27 may be, for example KDP and have a thickness of about 30 microns to a couple of millimeters. Other crystals which may be used are KTP, $KNO_3$, $LiIO_3$, BBO, $LiN_6NO_3$ or any other nonlinear crystal having an $X^{(2)}$. The light emitted from crystal 27 is passed through an aperture 29 and then detected by a detector 31. Detector 31 may be a photomultiplier tube. The output of detector 31 is then processed (by means not shown). In use, one of the two beams from beamsplitter 13 is delayed relative to the other to obtain an intensity profile and from the intensity profile the pulse width is obtained.

As can be appreciated, dispersion is produced when the light is passed through beamsplitter 13, through lens 25 and through crystal 27. Also, if the mirrors are dielectrics, additional dispersion will be introduced.

The purpose of this invention is to minimize if not substantially eliminate such time dispersion (i.e. eliminate the delay and broadening).

Figure 2:
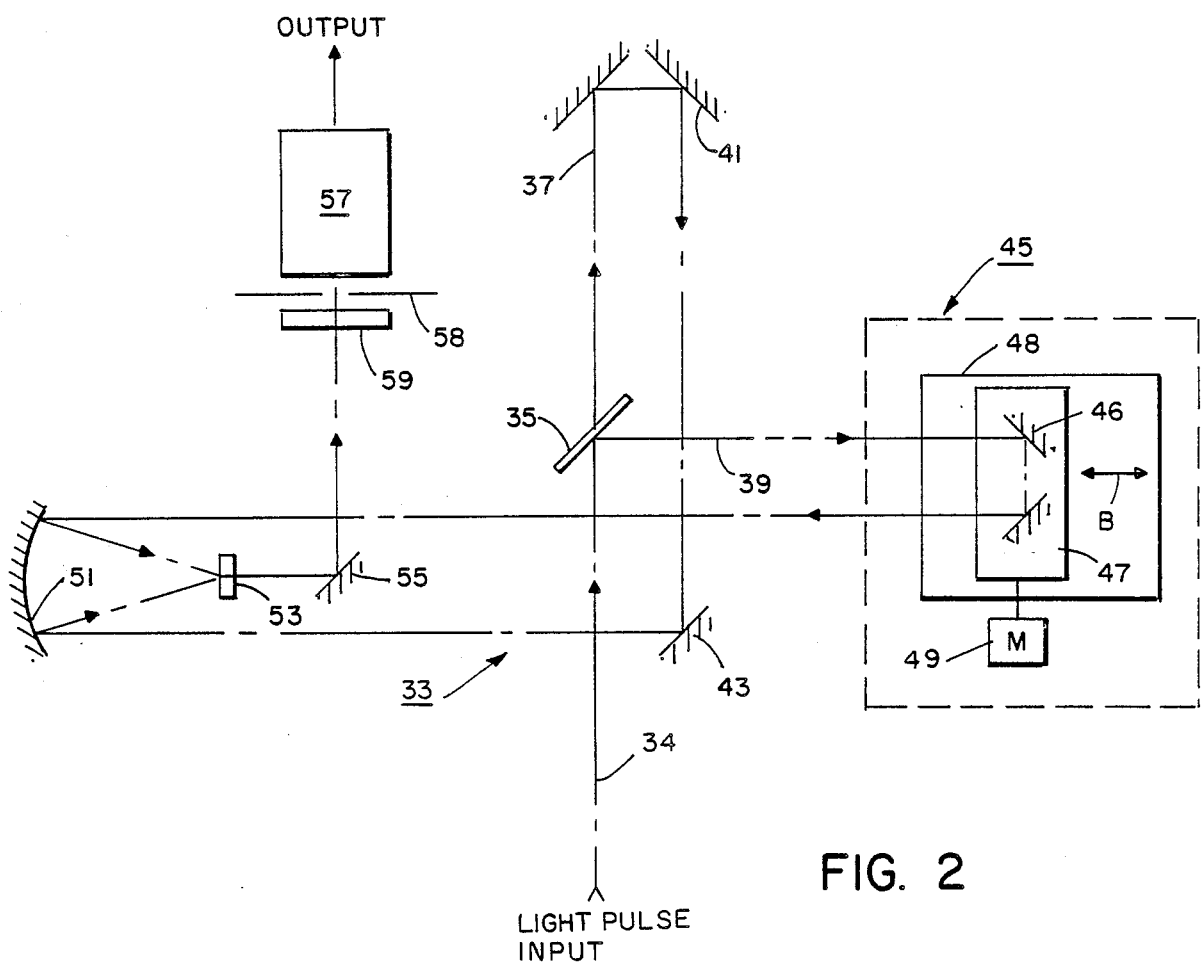
FIG. 2 is a schematic of a thin pellicle beamsplitter type SHG autocorrelator constructed according to the teachings of this invention.

Referring now to FIG. 2 there is shown an SHG autocorrelator constructed according to this invention and identified by reference numeral 33.

SHG autocorrelator 33 includes a beamsplitter 35 for splitting a pulse of light 34 (from a source, not shown) into a transmitted beam 37 and a reflected beam 39. Beamsplitter 35 is in the form of a thin pellicle. The thin pellicle may be for example about 2 to 5 microns thick. The transmitted beam 37 is passed through a first optical delay 41 which is stationary and is then deflected by a flat metal coated mirror 43. Optical delay 41 comprises a metal coated corner mirror 42 which functions as a delay and also serves to change the direction of transmitted beam 37. Mirror 43 serves to change the direction of the beam deflected off first corner mirror 41. The reflected beam 39 from beamsplitter 35 is reflected off a second optical delay 45 which is adjustable. Optical delay 45 which also serves to change the direction of the beam comprises a metal coated corner mirror 46 which is mounted on a support 47 which is mounted on a base 48. Support 47 is movable by a motor 49 in the direction shown by arrows B so that the optical path length of the reflected beam can be selectively changed. Motor 49 may be a stepper motor and support 47 a translation stage. Alternatively, a shaker mechanism may be employed to move mirror 46 back and forth in the direction of arrows B.

The light beam deflected off flat mirror 43 and the light beam deflected off second optical delay 45 are collected by a concave metal coated mirror 51 and brought to focus by mirror 51 in a thin SHG crystal 53. Crystal 53 is about 100 μm thick. Crystal 53 may be, for example KDP. Light emerging from crystal 53 is deflected off a flat mirror 55, which serves to change the direction of the emerging beam. The deflected beam is then detected by a detector 57 after passing through a bandpass filter 59. Detector 57 may be for example a photodetector. The output of detector 57 processed by means, not shown. Band pass filter 59 serves to pass only second harmonic generated light. An aperture 58 may be positioned in front of detector 57 to reduce noise and enhance the dynamic range.

Autocorrelator 33 is used in the same way as autocorrelator 11.

As can be seen, SHG autocorrelator 33 does not contain any lenses and the beamsplitter and SHG crystal are both thin. Also, all the mirrors are metal coated. Since the thin pellicle beamsplitter is on the order of about 2 to 10 microns thick, the dispersion produced by this element is negligble i.e. less than 0.2 fs (see table above). As to the SHG crystal, if it is made of KDP and is 100 μm thick and the pulse of light is 10 fs and centered at 620 nm with a 40 nm spread, the time delay (between the 600 nm pulse and the 640 nm pulse) because of dispersion using the formula: $\tau_{DELAY} = L(1.427 \times 10^{-11})$ sec is 1.43 fs, which is negligble. The time broadening for 100 m for a pulse of $\tau_D = 10$ fs with the center wavelength at 6.20 nm because of dispersion using the formula $$\tau_{\frac{1}{2}}(L) = \sqrt{\tau_0^2 + \tau_D^2}$$

is 0.56 fs for the 600 nm pulse and 0.51 fs for the 640 nm pulse which is also negligble. The $\tau_D$ is 1.645 for a 620 nm pulse and the value of $\tau_{\frac{1}{2}}(100\mu)$ is 10.13 fs.

Thus, the effects of dispersion in SHG autocorrelator 33 are negligble if the L (i.e. thickness) is less than 100μ, for 10 fs pulses.

Figure 3:
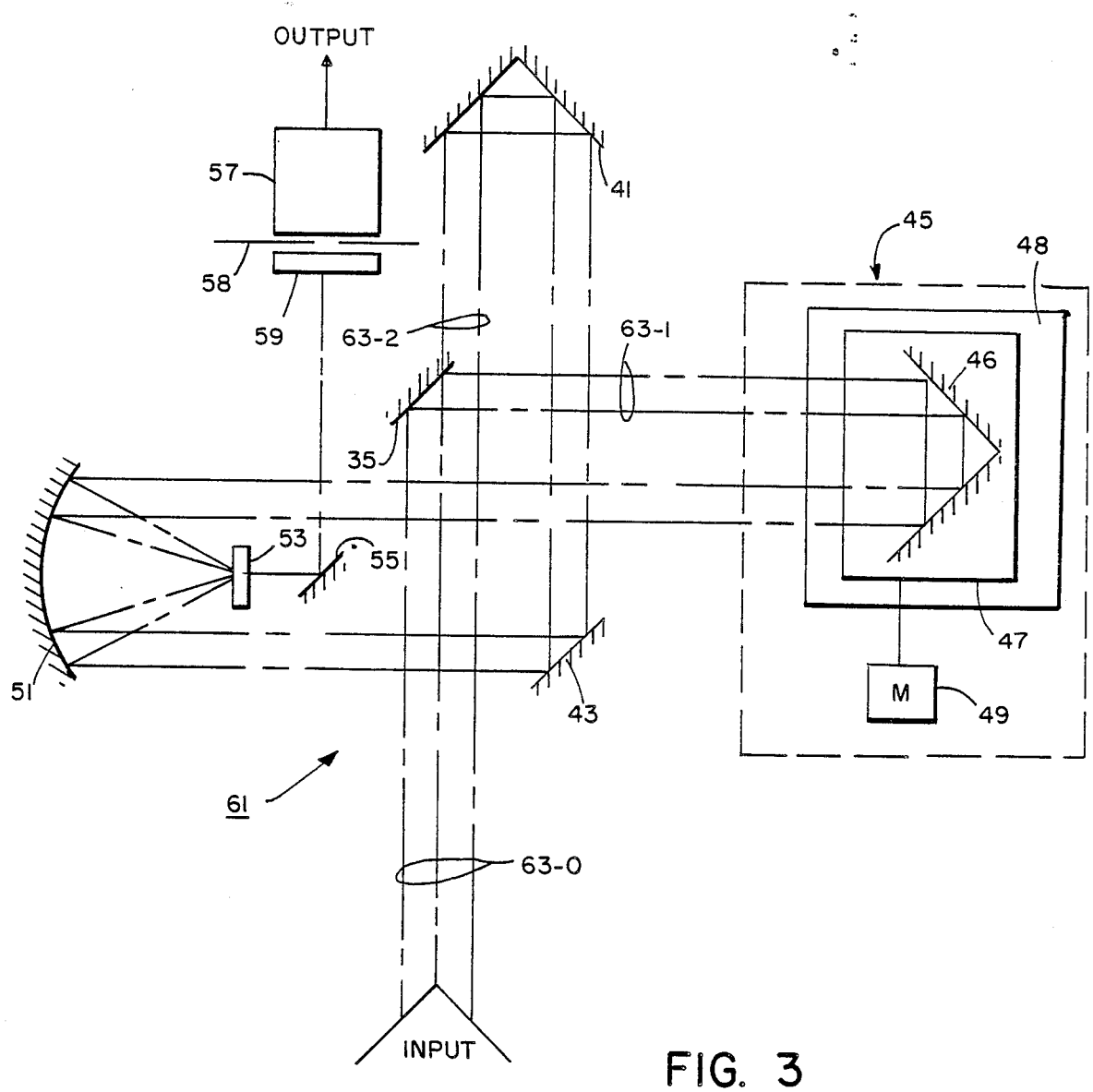
FIG. 3 is a schematic of a flat mirror beamsplitter type SHG autocorrelator constructed according to the teachings of this invention.

Referring now to FIG. 3 there is shown another embodiment of the invention, the embodiment being identified by reference numeral 61. Apparatus 61 differs from apparatus 33 only in that thin pellicle beamsplitter 35 is replaced by flat metal coated mirror 63 which is positioned so as to receive one half of the input pulse 63-0 and thereby split the input pulse 63-0 into two beams 63-1 and 63-2.

Figure 4:
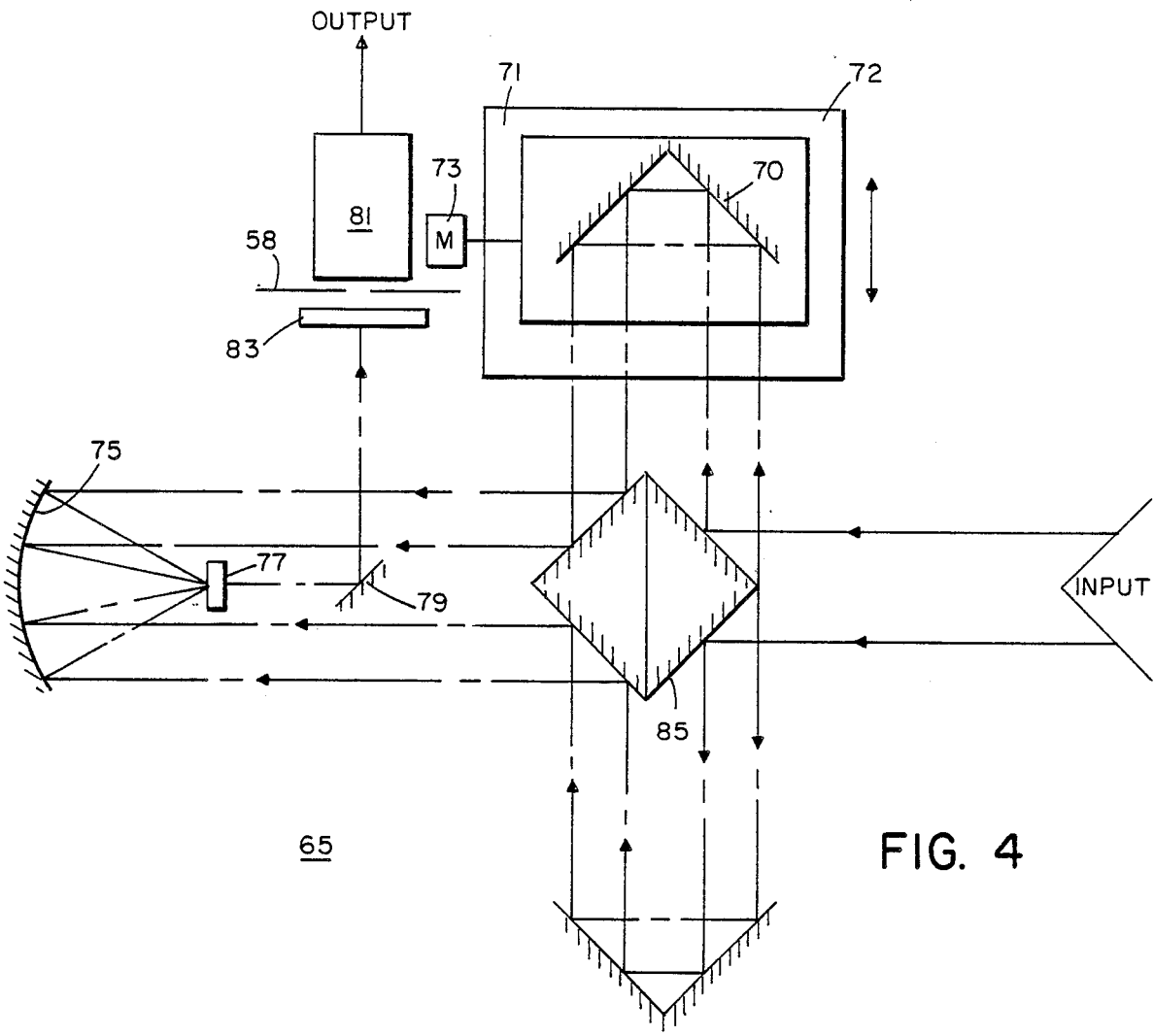
FIG. 4 is a schematic of a mirror coated corner cube type SHG autocorrelator constructed according to the teachings of this invention.

Referring now to FIG. 4 there is shown another embodiment of the invention, the embodiment being identified by reference numeral 65. Embodiment 65 is similar to the FIG. 2 embodiment in that it includes an aperture 58, an optical delay 67 in the form of a metal mirror coated corner cube which is stationary, an adjustable optical delay 69 in the form of a metal mirror coated corner cube 70 mounted on a support 71 and movable on a base 72 by a motor 73, a concave metal coated mirror 75, an SHG crystal 77, a flat mirror 79, a photodetector 81 and a bandpass filter 83. However, instead of the beamsplitter to split the pulse into two beams, there is a metal mirror coated corner cube 85. In addition, flat mirror 43 is eliminated. As can be seen, the input pulse is split into two beams by corner cube 85.

One beam is deflected off of corner cube 67 while the other beam is deflected off corner cube 69. The two beams are then collected by the concave mirror 75 as in the FIG. 2 embodiment.

Figure 5:
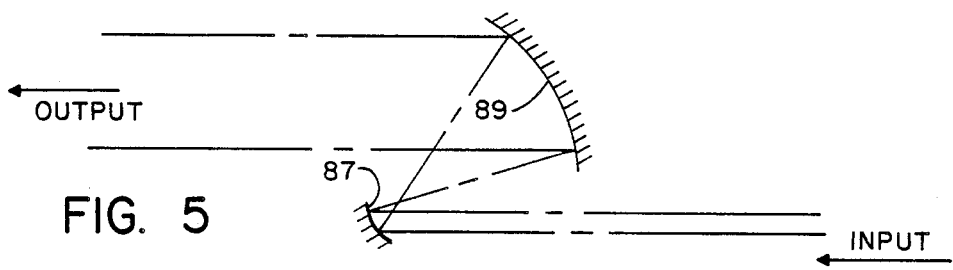
FIGS. 5 and 6 are views of two different types of beam size controllers which may be used with the SHG autocorrelator of this invention.
Figure 6:
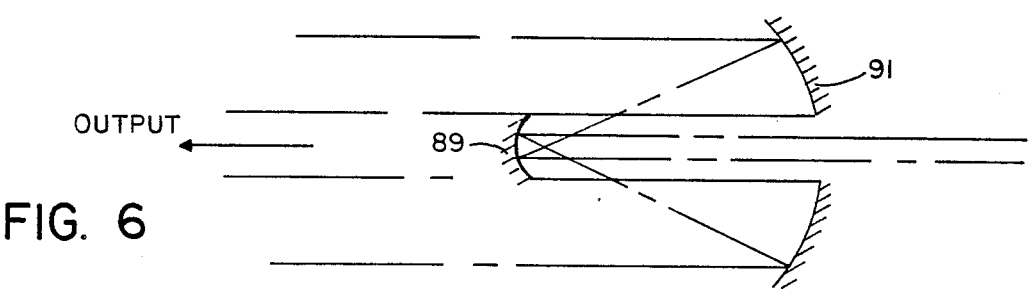

In FIGS. 5 and 6 are shown two different arrangements for enlarging the size of the input laser pulse, for use for example, with the FIGS. 3 and 4 embodiments, without the use of dispersive media. FIG. 5 shows an off-axis arrangement including two concave metallic mirrors 87 and 89 while FIG. 6 shows an on-axis arrangement comprising two concave metallic mirrors 89 and 91. As can be seen, both versions change the beam size without going through any dispersive media.

The use of metal coated mirror optics (as opposed to dielectric mirrors) reduces time dispersion on reflection to less than 0.1 fs.

The embodiments of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An SHG autocorrelator for use in measuring the duration of an ultrashort pulse of light comprising:
   a. means for splitting the pulse of light into first and second beams,
   b. a first optical delay disposed along the path of the first beam,
   c. a second optical delay disposed along the path of the second beam, said second optical delay being movable,
   d. an SHG crystal,
   e. curved mirror means for bringing the first and second beams to focus in the SHG crystal, and
   f. detector means for detecting second harmonic generated light emitted from the SHG crystal.

2. The SHG autocorrelator of claim 1 and wherein the curved mirror means comprises a concave mirror.

3. The SHG autocorrelator of claim 1 and wherein the means for splitting the pulse of light into first and second beam comprises a thin pellicle beamsplitter.

4. The SHG autocorrelator of claim 1 and wherein the means for splitting the pulse of light into first and second beams comprises a reflective coated corner cube.

5. The SHG autocorrelator of claim 1 and wherein the means for splitting the pulse of light into first and second beams comprises a flat mirror.

6. The SHG autocorrelator of claim 1 and further including bandpass filter means disposed between the detector means and the SHG crystal for filtering out light other than the second harmonic generated light.

7. The SHG autocorrelator of claim 1 and wherein the SHG crystal is KDP, LiO$_3$, KNO$_3$, KTP, BBO or LiN$_6$NO$_3$.

8. The SHG autocorrelator of claim 1 and wherein the SHG crystal is a thin crystal.

9. The SHG autocorrelator of claim 1 and wherein the first optical delay means comprises a corner mirror.

10. The SHG autocorrelator of claim 1 and wherein the second optical delay means comprises a corner mirror.

11. The SHG autocorrelator of claim 1 and wherein the curved mirror means is a metallic coated mirror.

12. The SHG autocorrelator of claim 1 and further including an aperture to reduce noise.

13. The SHG autocorrelator of claim 1 and wherein the SHG crystal is any nonlinear crystal having a $X^{(2)}$.

14. The SHG autocorrelator of claim 1 and wherein the second optical delay includes a motor.

15. The SHG autocorrelator of claim 14 and wherein the second optical delay includes a shaker.

16. The SHG autocorrelator of claim 14 and wherein the second optical delay includes a stepper motor.

17. The SHG autocorrelator of claim 1 and wherein the first optical delay comprises a corner cube.

18. The SHG autocorrelator of claim 1 and wherein the thin crystal has a thickness of about 20 to 500 microns.

* * * * *